United States Patent [19]

Arduengo, III

[11] Patent Number: 5,182,405
[45] Date of Patent: Jan. 26, 1993

[54] PREPARATION OF 1,3-DISUBSTITUTED IMIDAZOLIUM SALTS

[75] Inventor: Anthony J. Arduengo, III, Wilmington, Del.

[73] Assignee: E. I. Du Pont de Nemours and Company, Wilmington, Del.

[21] Appl. No.: 761,556

[22] Filed: Sep. 18, 1991

Related U.S. Application Data

[62] Division of Ser. No. 500,831, Mar. 29, 1990, Pat. No. 5,077,414.

[51] Int. Cl.$^5$ .................. C07D 233/56; C07D 233/58
[52] U.S. Cl. ........................... 548/335.1; 548/343.1
[58] Field of Search ........................ 548/335, 341

[56] References Cited

U.S. PATENT DOCUMENTS 4,450,277  5/1984  Graf et al. .................... 548/346

OTHER PUBLICATIONS

Windmueller et al., J. Biol. Chem., vol. 234, pp. 895–899 (1959).
Benac, B. L.; Burgess, E. M.; Arduengo, A. J., III Org. Syn., vol. 64, p. 92 (1986).
Rothenberg, A. S.; Ballentine, F. A.; Panzer, H. P., Polym. Mater. Sci. Eng., vol. 57, p. 134 (1987).
Zettlitzer, M.; tom Dieck, H.; Haupt, E. T. K.; Stamp, L., Chem. Ber., vol. 119, p. 1868 (1986).
Wanzlick, H.; Schönherr, H., Angew. Chem., Int. Ed. Engl., vol. 7, p. 141 (1968).
Wanzlick, H.; Schönherr, H., Chem. Ber., vol. 103, p. 1037 (1970).
Wanzlick, H.; Schönherr, H., Justus Liebigs Ann. Chem., vol.731, p. 176 (1970).
Bedford, C. D. et al., J. Med. Chem., vol. 32, pp. 504–516 (1989).

Primary Examiner—Floyd D. Higel
Assistant Examiner—Lenora Miltenberger
Attorney, Agent, or Firm—Nancy S. Mayer

[57] ABSTRACT

A process for the preparation of 1,3-disubstituted imidazolium salts that comprises reaction of an α-dicarbonyl compound, an aldehyde, an amine and an acid is disclosed.

3 Claims, No Drawings

PREPARATION OF 1,3-DISUBSTITUTED IMIDAZOLIUM SALTS

This is a division of application Ser. No. 07/500,831, filed Mar. 29, 1990, now U.S. Pat. No. 5,077,414.

FIELD OF THE INVENTION

The present invention provides a novel one-step process for the preparation of 1,3-disubstituted imidazolium salts. The process involves reaction of an α-dicarbonyl compound, an amine, an aldehyde and an acid.

BACKGROUND OF THE INVENTION 1,3-Disubstituted imidazolium salts have been prepared by direct substitution on an imidazole unit. For example, 1-substituted imidazoles have been alkylated in the 3 position [Benac, B. L.; Burgess, E. M.; Arduengo, A. J., III Org. Syn., Vol. 64, page 92 (1986)]. This alkylation process is limited to the preparation of 1,3-disubstituted imidazolium salts for which a 1-substituted imidazole precursor is available and this imidazole precursor must be synthesized in a prior step.

Double alkylation on 1,3-disubstituted imidazoles has also been reported [Rothenberg, A. S.; Ballentine, F. A.; Panzer, H. P. Polym. Mater. Sci. Eng., Vol. 57, page 134 (1987)]. This process requires a previously formed imidazole as a starting material.

1,3-Disubstituted imidazolium salts have also been prepared by the condensation of 2 equivalents of a bis(imine) in the presence of an acid catalyst [Zettlitzer, M.; Tom Dieck, H.; Haupt, E. T. K.; Stamp, L. Chem. Ber., Vol. 119; page 1868 (1986)]. This condensation route causes the loss of one equivalent of a primary amine so that not all the available functionality can be utilized. Additionally the substituent in the 2-position of the final imidazolium salt must be derived in subsequent steps from an imine.

1,3-Disubstituted imidazole-2-thiones have been desulfurized to produce 1,3-disubstituted imidazolium salts [Wanzlick, H.; Schönherr, H. Angew. Chem., Int. Ed. Engl., Vol. 7, page 141 (1968): Wanzlick, H.; Schönherr, H. Chem. Ber., Vol. 103, page 1037 (1970): Wanzlick, H.; Schönherr, H. Justus Liebigs Ann. Chem., Vol. 731, page 176 (1970)]. This desulfurization route requires additional steps to synthesize the penultimate imidazole-2-thione and only imidazolium salts which bear a hydrogen in the 2-position can be prepared.

Imidazoles which bear no substituents in the 3-position have been synthesized from the reaction of an α-dicarbonyl compound, ammonia, an aldehyde, and a primary amine [Graf, F.; Hupfer, L.; U.S. Pat. No. 4,450,277 issued May 22, 1984]. Through this process it is not possible to synthesize imidazolium salts since there is no acid included to provide a counterion to the imidazolium group.

It is the object of this invention to provide a simple one step process for preparation of 1,3-disubstituted imidazolium salts from readily available starting materials.

SUMMARY OF THE INVENTION

The present invention comprises a process for the preparation of a 1,3-disubstituted imidazolium salt comprising contacting an α-dicarbonyl compound of formula

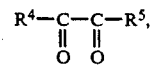

an aldehyde of the formula $R^2CHO$, one or more amines of the formula $R^1NH_2$, and an acid of the formula $H_nX$, wherein: each $R^1$ is hydrocarbyl, or substituted hydrocarbyl; $R^4$ and $R^5$ are each independently hydrogen, hydrocarbyl or substituted hydrocarbyl; X is an anion; and n is an integer corresponding to the number of anionic charges on X. The present invention further comprises novel 1,3-disubstituted imidazolium salts.

DETAILED DESCRIPTION OF THE INVENTION

This invention comprises a process for the preparation of 1,3-disubstituted imidazolium salts having the following formula:

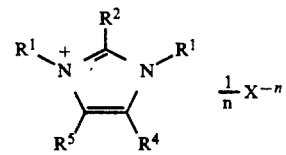

wherein:
each $R^1$ is independently hydrocarbyl or substituted hydrocarbyl;
$R^2$, $R^4$, and $R^5$ are each independently hydrogen, hydrocarbyl, or substituted hydrocarbyl;
X is an anion; and
n is an integer corresponding to the number of anionic charges on X.

The term "substituted hydrocarbyl" is used herein to mean any substituent which does not interfere with the reaction or render the product unstable. For example, suitable substituents include, but are not limited to, ether, ester, halo, tertiary amino, hydroxy, vinyl, and acetylenic.

From this process, 1,3-disubstituted imidazolium cations are obtained as salts in which the anionic portion is derived from the conjugate base of the acid used in the process. Thus hydrochloric acid yields an imidazolium chloride from the process, while sulfuric acid yields an imidazolium sulfate or bisulfate.

Alpha-dicarbonyl compounds of formula

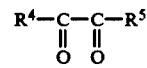

useful in the process of the present invention are readily commercially available. In preferred α-dicarbonyl compounds $R^4$ and $R^5$ are each independently hydrogen, an alkyl group of 1 to 4 carbon atoms, or phenyl, or together $R^4$ and $R^5$ form a cyclohexane group. Especially preferred α-dicarbonyl compounds are those wherein $R^4$ and $R^5$ are each independently hydrogen or methyl.

Aldehydes of the formula $R^2CHO$ useful in the present process are also readily commercially available. Preferred aldehydes are those wherein $R^2$ is hydrogen, an alkyl group containing 1 to 4 carbon atoms, or phenyl. Especially preferred aldehydes are those wherein $R^2$ is hydrogen or methyl. Also suitable for use herein are compounds that readily form aldehydes under the reaction conditions of the instant process. For example, formaldehyde may be added as aqueous formaldehyde solution, or as paraformaldehyde, s-trioxane or plyoxymethylene.

Amines suitable for use herein include those of formula $R^1HN_2$ wherein $R^1$ is hydrocarbyl, or substituted hydrocarbyl. Preferred amines are those wherein $R^1$ is an alkyl group containing 1 to 4 carbon atoms, 2-hydroxyethyl, phenyl, or 4,4,5,5,6,6,7,7,8,8,9,9,10,10,11,11,11-heptadecafluoroundecyl. It is preferred to use one amine in the process of the present invention.

When more than one amine is used, the following combinations are preferred: methylamine and n-propylamine, methylamine and isopropylamine; methylamine and n-butylamine; methylamine and isobutylamine; methylamine and aniline.

Although weaker acids are operative in the process of the present invention, protic acids with a pKa of less than about 6 are believed to give superior results. Preferred acids have a pKa of less than about 4. Especially preferred acids have a pKa of less than about 2. The pKa's discussed herein are measured in water. Examples of acids useful in the process of the present invention include, but are not limited to, carboxylic acids such as acetic acid, benzoic acid and stearic acid; other organic acids such as benzenesulfonic acid or phenylphosphonic acid; and inorganic acids such as HF, HCl, HBr, HI, $H_2SO_4$ or $H_3PO_4$. Especially preferred acid species are HF, HCl, HBr, HI, $H_2SO_4$ or $H_3PO_4$. It will be appreciated by those skilled in the art that the anion X in the product 1,3-disubstituted imidazolium salt is derived from the acid. The acid used in this process should act only as an acid. For example, some acids are also strong oxidizing agents and would destroy one or more of the starting materials or products by oxidation. Such otherwise reactive acids should be avoided.

Since water is produced in the process of the present invention, compounds that are not acids themselves, but can react with water to form acids, are also suitable for use as acid substitutes and are encompassed within the meaning of the term "acid" as used herein. Examples of such compounds include, but are not limited to, boron halides, silicon halides, readily hydrolyzable sulfonate or phosphate esters, and the like.

The α-dicarbonyl, aldehyde, amine and acid reactants are advantageously employed in a molar ratio of 1:1:2:1, respectively. The amine reactant may be single amine or a mixture of different amines. When the amines are used as a mixture, the total molar equivalents should be 2. For example, 2 equivalents of a 1:1 molar mixture of two unique amines may be used in place of the 2 equivalents of a single amine. Variation of this molar reaction ratio is possible but may result in the incomplete consumption of some of the starting materials.

In the process of the present invention, it is possible to combine the reactants in any order to facilitate ease of addition or handling. For example the acid ($H_nX$) may be combined with the amine ($R^1NH_2$) to form a primary ammonium salt ($R^1NH_3^+1/_nX^{-n}$) which can be used in the process. Alternatively, one mole of amine can be mixed with one mole of the aldehyde, then another mole of amine and the acid added, and finally the α-dicarbonyl compound added. This alternative is convenient to control the temperature of the process. The examples illustrate these alternatives.

It will be appreciated by those skilled in the art that when $R^4$ and $R^5$ are different and more than one amine is used, more than one isomeric product may be produced. In Example 3 hereinafter, a mixture of three possible isomeric products is obtained.

The process of this invention can be carried out between from about $-10°$ to about 200° C., preferably from about 20° to about 100° C., and most preferably from about 20° to about 80° C. The reaction can be quite exothermic and efficient cooling may be required to maintain the temperature in an optimal range. The process is believed to be an equilibrium reaction which produces water. Therefore to drive the reaction to completion it may be desirable to remove the water formed or initially present in the reaction. This can be conveniently done by evaporation or azeotropic distillation.

Although not required, a solvent may be used in this process. Any inert organic solvent, or water, or a combination thereof, is suitable for use herein. It is not necessary for the reactants to be completely soluble in the solvent(s) used, but the reactants should be slightly insoluble. The product can be soluble or insoluble in the solvent used. Examples of suitable solvents include, but are not limited to, toluene or water.

Reaction times typically range from about 0.5 to about 24 hours, usually from about 1 to about 4 hours. Although not required it is preferred to exclude oxygen to avoid oxidation of the starting materials. It is convenient to exclude oxygen by using an inert atmosphere such as nitrogen or argon. Agitation, especially when the reaction is heterogeneous, is desirable. The product may be isolated by methods well known to those skilled in the art, such as by evaporation of the solvent.

The 1,3-disubstituted imidazolium salts thus produced have utility as synthetic intermediates [Benac, B. L.; Burgess, E. M.; Arduengo, A. J., III Org. Syn., Vol. 64, page 92 (1986)], polymer precursors [Rothenberg, A. S.; Ballentine, F. A.; Panzer, H. P. Polym. Mater. Sci. Eng., Vol. 57, page 134 (1987)] and pharmaceuticals [Bedford, C. D.; Harris, R. N., III; Howd, R. A.; Goff, D. A.; Koolpe, G. A.; Petesch, M.; Koplovitz, I.; Sultan, W. E.; Musallam, H. A. J. Med. Chem., Vol. 32, page 504 (1989)] among other applications.

A further aspect of the present invention is novel 1,3-disubstituted imidazolium compounds of the formula

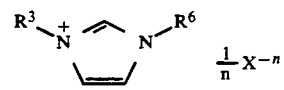

wherein $R^3$ and $R^6$ are both n-propyl, isobutyl, 2-hydroxyethyl; or 4,4,5,5,6,6,7,7,8,8,9,9,10,10,11,11,11-heptadecafluoroundecyl, or $R^3$ is methyl and $R^6$ is n-propyl;

X is an anion; and n is an integer corresponding to the number of anionic charges on X.

These compounds are prepared using the process of the present invention as described above using the appropriate amines, acetaldehyde, glyoxal and an acid. The utility of these compounds is as previously described for the 1,3-disubstituted imidazolium salts produced by the above described process. Preferred anions X are halides, sulfate, bisulfate, phosphate, hydrogen phosphate, and dihydrogen phosphate. A preferred imidazolium salt is when $R^6$ in the above compound is n-propyl and $R^3$ is methyl.

EXAMPLE 1

Isopropylamine, 17.73 grams (0.3 mol), was added dropwise over 20 min. to a suspension of paraformaldehyde, 9.01 grams (0.3 mol), in 50 ml of toluene at such a rate that the temperature did not exceed 40° C. When the addition was complete, the mixture was stirred for an additional 10 min. The mixture was then cooled to 3° C. by means of an ice bath. Isopropylamine, 17.73 grams (0.3 mol), was added in a slow steady stream to the cooled mixture. When the second isopropylamine addition was complete, 50 ml of aqueous 6N HCl (0.3 mol) was added dropwise over 30 min. to the reaction mixture. By means of an ice bath, the reaction temperature was held below 20° C. When the HCl addition was complete, the ice bath was removed and the solution was warmed to 25° C. At this temperature, 43.53 grams (0.3 mol) of 40% aqueous glyoxal was added. When the glyoxal addition was complete the reaction mixture was stirred for an additional 1 h. An additional 45 ml of toluene was added to the reaction mixture and water, 73.68 grams, was removed from the reaction mixture by azeotropic distillation (Dean Stark trap) with the toluene. Removal of volatiles under vacuum yielded 56.43 grams (99% of theory) of 1,3-diisopropylimidazolium chloride. $^1$H NMR (CD$_3$CN) of the material showed only resonances at δ 1.55 (d, $^3J_{HH}$=6.8 Hz, 2 H); 4.70 (sept., $^3J_{HH}$=6.8 Hz, 12 H); 7.66 (d, $^4J_{HH}$, =1.6 Hz, 2 H); 9.89 (t, $^4J_{HH}$, 1.6 Hz, 1 H) consistent with the desired product.

EXAMPLE 2

Propylamine, 17.73 grams (0.3 mol), was added dropwise over 20 min. to a suspension of paraformaldehyde, 9.01 grams (0.3 mol), in 50 ml of toluene at such a rate that the temperature did not exceed 40° C. When the addition was complete, the mixture was stirred for an additional 10 min. The mixture was then cooled at 4° C. by means of an ice bath. Propylamine, 17.73 grams (0.3 mol), was added in a slow steady stream to the cooled mixture. When the second isopropylamine addition was complete, 50 ml of aqueous 6N HCl (0.3 mol) was added dropwise over 30 min. to the reaction mixture. By means of an ice bath, the reaction temperature was held below 25° C. When the HCl addition was complete, the ice bath was removed and the solution was warmed to 25° C. At this temperature, 43.53 grams (0.3 mol) of 40% aqueous glyoxal was added. When the glyoxal addition was complete the reaction mixture was stirred for an additional 1 h. An additional 45 ml of toluene was added to the reaction mixture and water, 78.18 grams, was removed from the reaction mixture by azeotropic distillation (Dean Stark trap) with the toluene. Removal of volatiles under vacuum yielded 58.02 grams (102% of theory) of 1,3-diisopropylimidazolium chloride. $^1$H NMR (CD$_3$CN) of the material showed only resonances at δ 0.90 (t, $^3J_{HH}$=7.4 Hz, 6 H); 1.88 (tt, 4 H); 4.27 (t, $^3J_{HH}$=7.4 Hz, 4 H); 7.75 (d, $^4J_{HH}$=1.6 Hz, 2 H); 9.47 (t, $^4J_{HH}$, =1.6 Hz, 1 H) consistent with the desired product.

EXAMPLE 3

Propylamine, 9.84 grams (166.5 mmol) was added dropwise to a suspension of paraformaldehyde, 5.0 grams (166.4 mmol) in 25 ml of toluene. The reaction was kept cool in a cold water bath. When the addition was complete, the mixture was stirred for 15 min. Methylamine hydrochloride, 11.24 grams (166.5 mmol) was introduced in several small portions and the reaction mixture was stirred for 10 min after the addition. Glyoxal, 24.2 grams (166.5 mmol) of 40 wt % aqueous solution was added dropwise to the reaction mixture. By means of an oil bath the reaction temperature was held below 40° C. When the addition was complete, the reaction mixture was heated to 90° C. by means of a hot oil bath. The reaction mixture was maintained at 90° C. for 1.5 h. By means of a Dean Stark trap, filled with toluene, the water (23.3 ml) was azeotroped out of the reaction. This reaction produced a 1:1:2 molar mixture of 1,3-dimethylimidazolium chloride, 1,3-dipropylimidazolium chloride, and 1-methyl-3-propylimidazolium chloride, respectively.

EXAMPLE 4

A solution of p-toluidine, 10.72 grams (100 mmol) in of 15 ml toluene, was added dropwise over 10 min. to a suspension of paraformaldehyde, 1.51 grams (50 mmol), in 15 ml of toluene. When the addition was complete, the mixture was heated to 100° C., dissolving all of the solids. When the mixture had cooled to 40° C., 8.3 ml of aqueous 6N HCl (50 mmol) was slowly added to the reaction mixture. When the addition was complete, the mixture was stirred for 5 min. before 7.25 grams (50 mmol) of 40% aqueous glyoxal was added. When the glyoxal addition was complete the reaction mixture was stirred for 5 min. at room temperature, then heated to 100° C. in an oil bath and maintained at that temperature for 2 hours. A dark solid formed while the reaction mixture was hot. The reaction mixture was then removed from the heat and allowed to cool to room temperature. Removal of volatiles under vacuum yielded a dark oily solid. The solid was triturated in acetonitrile and 5.0 grams of dark solid was filtered off. $^1$H NMR (CD$_3$OD) of the product showed resonances at δ 2.46 ppm (s, 6H); 7.48 (d, $^3J_{HH}$=8.5 Hz, 4 H, Ar); 7.71 (d, $^3J_{HH}$=8.5 Hz, 4 H, Ar); 8.24 (d,$^4J_{HH}$, =1.6 Hz, 2 H); 10.01 (t, $^4J_{HH}$, =1.6 Hz, 1 H), consistent with the desired 1,3-bis(p-tolyl)imidazolium chloride. An additional 9.94 grams of material was isolated by rotary evaporation of the filtrate. Total yield was 105% of theory.

What is claimed is:

1. A compound represented by the formula

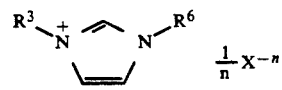

wherein:

R$^3$ and R$^6$ are both n-propyl, isobutyl, or 4,4,5,5,6,6,7,7,8,8,9,9,10,10,11,11,11-heptadecafluoroundecyl; or R$^3$ is methyl and R$^6$ is n-propyl;

X is an anion; and n is an integer corresponding to the number of anionic charges on X.

2. A compound of claim 1 wherein R$^3$ is n-propyl and R$^6$ is methyl.

3. A compound of claim 1 wherein X is a halide, sulfate, bisulfate, phosphate, hydrogen phosphate, or dihydrogen phosphate.